United States Patent [19]
Woolley

[11] 3,933,440
[45] Jan. 20, 1976

[54] CHEMICAL REACTION VESSEL
[75] Inventor: John Frederick Woolley, Sawbridgeworth, England
[73] Assignee: International Telephone and Telegraph Corporation, New York, N.Y.
[22] Filed: Aug. 12, 1974
[21] Appl. No.: 496,569

[30] Foreign Application Priority Data
Sept. 20, 1973 United Kingdom............... 44086/73

[52] U.S. Cl............... 23/259; 23/252 R; 23/253 R; 23/292; 215/6
[51] Int. Cl.² .. B01L 1/00; B01L 7/00; G01N 33/38
[58] Field of Search...... 23/259, 292, 252 R, 253 R; 215/6

[56] References Cited
UNITED STATES PATENTS
726,982  5/1903  Park......................................... 215/6
1,262,081  4/1918  Mojonnier........................... 23/292
3,705,661  12/1972  Davis....................................... 215/6
3,773,468  11/1973  Hubbard et al...................... 23/259
3,859,671  1/1975  Tomasello........................... 215/6 X Primary Examiner—Joseph Scovronek
Assistant Examiner—Barry I. Hollander
Attorney, Agent, or Firm—James B. Raden; Harold J. Holt

[57] ABSTRACT

A gas-tight chemical reaction vessel for the chemical analysis of an intractable material such as glass. The reaction vessel comprises a body having at least two concentric chambers, one of which is adapted to contain a reagent, at least one other of which is adapted to receive a sample cap which in turn is adapted to receive a sample. The reaction vessel has a sealing member for sealing the chambers of the body and a cap for securing the sealing member against the body. The body, sealing member and sample cap are made of a material, desirably polytetrafluoroethylene, which is chemically inert to the reagents.

5 Claims, 2 Drawing Figures

CHEMICAL REACTION VESSEL

This invention relates to apparatus for the chemical analysis of intractable materials.

The dissolution of materials for chemical analysis is often difficult due to the nature of the material. Glasses in particular which contain a substantial proportion of silicon dioxide may be classed as very difficult. Such glasses can be dissolved by treatment with a reagent, such as hydrofluoric acid alone or hydrofluoric acid in admixture with a mineral acid, or by fusion above 900°C with an alkaline material.

Where analysis is required to determine trace impurities (parts per million or parts per billion), it is important that the corresponding impurity introduced by the reagent and by the apparatus be only a small part of the total impurity concentration.

According to this invention there is provided a gas-tight chemical reaction vessel, including a body member having a first chamber for reagents and at least one sample chamber, a sample cap for each sample chamber, a sealing member for sealing to the body member, and a cap for securing the sealing member against the body, and in which the body, the sealing member and the sample cap are made of a material which is chemically inert to the reagents.

Figure 1:
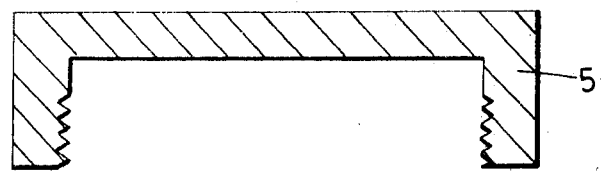
Figure 1:
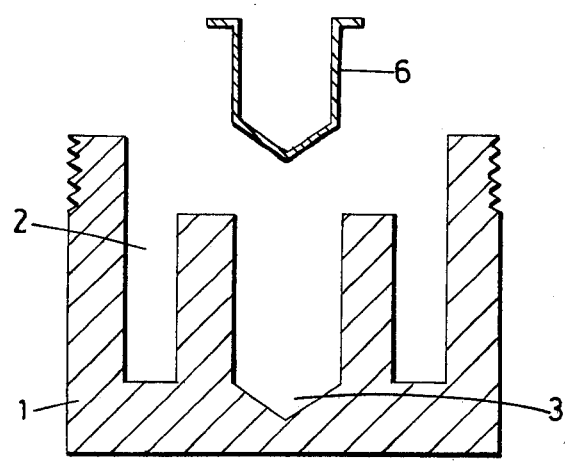
Figure 2:
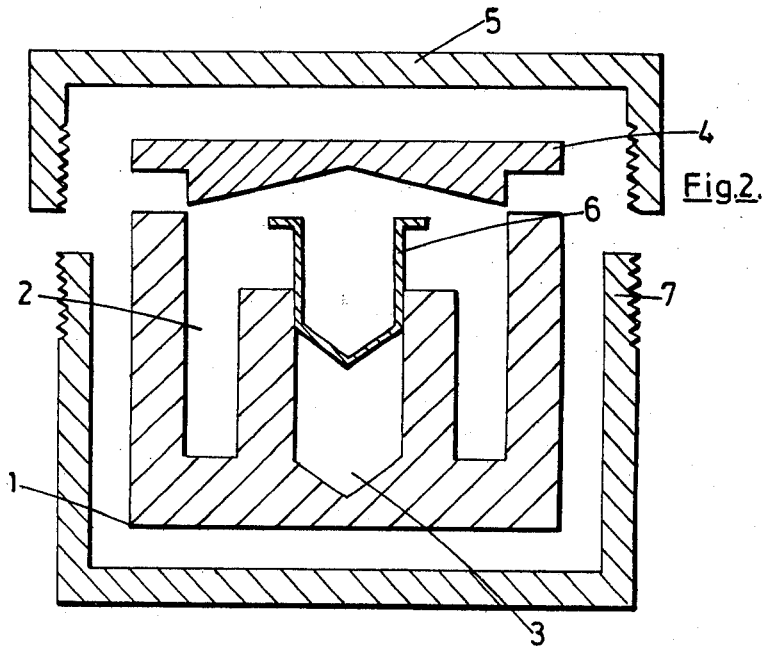

Embodiments of the invention will now be described with reference to the accompanying drawing in which FIG. 1 is an exploded cross section of a vessel for glass dissolution; and FIG. 2 is an alternative embodiment of the vessel of FIG. 1.

Referring to FIG. 1, the reaction vessel consists of a body 1 having concentric chambers 2 and 3, a sealing member 4 and a screw cap 5. The inner chamber 3 is adapted to contain a sample cap 6. The body 1, the seal 4 and the sample cap 6 are all made of polytetrafluoroethylene (PTFE) which is chemically inert to the reagents involved. The screw cap 5, however, may be made of aluminum alloy or other suitable material as it is not in contact with the reagents.

In use the glass sample, for example a soda-lime glass with iron as impurity, is crushed and placed in the sample cap 6 which is then placed in the inner chamber 3. The outer chamber 2 is filled with a mixture of hydrofluoric and nitric acids and the vessel is sealed and maintained at a temperature of 105° to 110°C for at least 4 hours. Under these conditions the acid mixture vaporizes within the sealed vessel to produce an atmosphere which is thermodynamically related to the chosen acid mixture and its temperature. The sample matrix undergoes attack by the acid vapour in accordance with the following general equation:

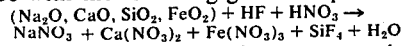
$(Na_2O, CaO, SiO_2, FeO_2) + HF + HNO_3 \rightarrow NaNO_3 + Ca(NO_3)_2 + Fe(NO_3)_3 + SiF_4 + H_2O$ It can be shown that if the correct ratio of nitric to hydrofluoric acid is chosen then the tendency will be towards the formation of the nitrates rather than the fluorides of the elements present. The important exception is silicon which forms a volatile fluoride which is absorbed into the acid on cooling thus effecting separation of silicon from the sample matrix.

Contamination of the sample by solvent acid mixture or its distillate is avoided as any condensate which forms on the inside of the seal 4 is directed to the outer acid chamber 2, and this movement is further assisted by the non-wetting properties of PTFE used in the construction of the vessel. The sample container 6 at the end of the reaction period therefore contains an uncontaminated water soluble mixture from which a large part of the sample matrix has been separated. The trace elements in the water soluble mixture can then be determined by known techniques.

Since the reaction is carried out by acid vapour in a sealed system contamination of the sample by solvent impurities and atmospheric impurities is greatly reduced compared with dissolution by acid solutions in open vessels. Furthermore, the use of ultra-high purity acids is not required as purification takes place in situ.

FIG. 2 shows an alternative embodiment of the vessel of FIG. 1. The arrangement is similar to that shown in FIG. 1 but the screw cap 5 is made of stainless steel, and the body 1 is enclosed in a stainless steel outer casing 7 to which the screw cap may be fitted. This vessel is suitable for use at temperatures up to 250°C and pressures of several atmospheres thus increasing the range of sample types which can be dissolved, for example rocks and ores.

The following Example illustrates the invention.

EXAMPLE 1

This example relates to the dissolution of a soda lime glass prior to the determination of trace metalic impurities by a modifid Atomic Absorption Spectroscope technique. A vessel as shown in FIG. 1 was employed. Between 50 and 100 mg of the finely powdered glass sample were weighed accurately into the sample cap 6 which was then placed in the inner chamber 3 of the vessel. A polypropylene pipette was used to introduce 3 ml of an acid mixture of 1 part nitric acid (S. G. 1.72) and 2 parts hydrofluoric acid 40% w/v HF) into the outer chamber 2. Both acids were Analytical Reagent grade. The seal 4 was placed in position and the vessel was sealed with the screw cap 5.

The vessel was maintained upright and placed in a hot air oven at 110°C for 4 hours after which it was allowed to cool to room temperature and the screw cap and seal were carefully removed. The sample cap 6 was removed from the inner chamber 3 and 2 ml double quartz distilled water was added. The mixture was stirred with a PTFE rod until all solids had dissolved thus providing a sample suitable for analysis by Atomic Absorption Spectroscopy.

It is to be understood that the foregoing description of specific examples of this invention is made by way of example only and is not to be considered as a limitation on its scope.

I claim:

1. A gas-tight chemical reaction vessel comprising a body member having a first chamber for reagents and at least one sample chamber, a sample cap within each sample chamber, said cap being adapted to contain a sample of intractable material, a sealing member for sealing the body member, and a cap for securing the sealing member against the body, said sealing member providing a gas-tight relationship with said body while retaining a vapor passageway between said first and said sample chambers, and in which the body, the sealing member and the sample cap are made of a material which is chemically inert to the reagents.

2. The reaction vessel of claim 1 in which the inert materials is polytetrafluoroethylene.

3. The reaction vessel of claim 1 which further includes an outer container to which the cap is secured to hold the sealing member against the body.

4. The reaction vessel of claim 1 in which the first chamber is concentric with the sample chamber.

5. The reaction vessel of claim 4 in which the inner surface of the sealing member is tapered from its center to it periphery so that it slopes downwardly toward the first chamber.

* * * * *